(12) United States Patent
Podolski

(10) Patent No.: US 8,519,004 B2
(45) Date of Patent: *Aug. 27, 2013

(54) DOSING REGIMES FOR TRANS-CLOMIPHENE

(75) Inventor: Joseph S. Podolski, The Woodlands, TX (US)

(73) Assignee: Repros Therapeutics Inc., The Woodlands, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/590,045

(22) Filed: Aug. 20, 2012

(65) Prior Publication Data

US 2012/0309839 A1 Dec. 6, 2012

Related U.S. Application Data

(63) Continuation of application No. 11/815,542, filed as application No. PCT/US2006/010022 on Mar. 17, 2006, now Pat. No. 8,247,456.

(60) Provisional application No. 60/664,290, filed on Mar. 22, 2005.

(51) Int. Cl.
*A61K 31/135* (2006.01)

(52) U.S. Cl.
USPC .......................................... 514/646

(58) Field of Classification Search
USPC ............................................ 514/646
See application file for complete search history.

(56) References Cited

U.S. PATENT DOCUMENTS 6,391,920 B1 * 5/2002 Fisch ........................... 514/648

FOREIGN PATENT DOCUMENTS

| WO | WO0191744 | * 12/2001 |
| WO | WO03005459 | * 1/2003 |

OTHER PUBLICATIONS

Mikkelson et al., Fertility and Sterility, 1986;46(3):392-396.*

* cited by examiner

*Primary Examiner* — San-Ming Hui
(74) *Attorney, Agent, or Firm* — Morgan, Lewis & Bockius LLP

(57) ABSTRACT

The present invention relates to the use of compositions comprising trans-clomiphene for treating men with hypogonadism. The invention is also directed to methods for treating males with hypogonadism and disorders related thereto, including reduction of muscle mass. limitation of body performance capacity, reduction of bone density, reduction of libido, reduction of potency, reduction of benign prostatic hyperplasia and infertility.

10 Claims, 7 Drawing Sheets

Normal Secretory Total Serum Testosterone Profiles in Healthy Young and Older Men Normal Secretory Total Serum Testosterone Profiles in Healthy Young and Older Men

DOSING REGIMES FOR TRANS-CLOMIPHENE

CROSS-REFERENCE TO RELATED APPLICATIONS

The present application is a continuation of U.S. application Ser. No. 11/815,542, filed Jan. 13, 2009, which is a national stage of International Application No. PCT/US2006/010022, filed Mar. 17, 2006, which claims the benefit of U.S. Provisional Patent Application No. 60/664,290, filed Mar. 22, 2005, the contents of which are incorporated herein by reference.

FIELD OF THE INVENTION

The present invention relates to the compositions and methods for treating male infertility. More specifically, the present invention relates to a composition comprising clomiphene enriched for trans-clomiphene, and methods of use thereof.

BACKGROUND

Testosterone is the primary male androgen, playing a vital role in overall male health. Testosterone is essential to the development and maintenance of specific reproductive tissues (testes, prostate, epididymis, seminal vesicle, and penis) and male secondary sex characteristics. It plays a key role in libido and erectile function and is necessary for the initiation and maintenance of spermatogenesis. Testosterone also has important functions not related to reproductive tissues. For example, it positively affects body composition by increasing nitrogen retention, which supports lean body mass, muscle size and strength. It also acts on bone to stimulate bone formation.

Testosterone secretion is the end product of a series of hormonal processes. Gonadotropin-releasing hormone (GnRH), which is secreted in the hypothalamus, controls the pulsatile secretion of luteinizing hormone (LH) and follicle stimulating hormone (FSH), which are secreted by the anterior pituitary. LH, in turn, regulates the production and secretion of testosterone in the Leydig cells of the testes, while FSH assists in inducing spermatogenesis.

Testosterone is most often measured as "total testosterone." This measurement includes testosterone that is bound to sex hormone-binding globulin (SHBG) (~44%) and is therefore not bioavailable and testosterone which either is free (~2%) or loosely bound to other proteins (non-SHBG-bound) (~54%).

Results from a WHO study indicate that testosterone is normally secreted in a circadian rhythm, with higher levels in the morning and nadir levels occurring around 8 to 10 p.m. See FIG. 1. This variation in testosterone secretion throughout the day becomes much less pronounced in older men (mean age equals 71 years). The importance of this rhythm is not known at this time.

Samples were obtained from both young and elderly patients every 10 minutes for 24 hours via an indwelling cannula. According to Tenover (1987) the mean 24 hr total serum testosterone levels in healthy young men (age range 22 yrs.-35 yrs. mean 27.3 yrs) was 4.9±0.3 (±SEM) mg/ml (17.0 nmol/L) while older men (age range 65 yrs-84 yrs. mean 70.7 yrs.) had a significantly lower mean 24 hrs. total serum testosterone level of 4.1±0.4 mg/ml. (P<0.5; 14.2 nmol/L).

Total serum testosterone levels obtained from single random samples were also significantly lower in older men (4.0±0.2 mg/ml [13.9 n nmol/L]) as compared to 4.8±0.2 mg/ml [16.6 nmol/L] in healthy young men.

Testosterone deficiency can result from underlying disease or genetic disorders and is also frequently a complication of aging. For example, primary hypogonadism results from primary testicular failure. In this situation, testosterone levels are low and levels of pituitary gonadotropins (LH and FSH) are elevated. Secondary hypogonadism is due to inadequate secretion of the pituitary gonadotropins. In addition to a low testosterone level, LH and FSH levels are low or low-normal. Some of the sequelae of adult testosterone deficiency include a wide variety of symptoms including: loss of libido, erectile dysfunction, oligospermia or azoospermia, absence or regression of secondary sexual characteristics, progressive decrease in muscle mass, fatigue, depressed mood and increased risk of osteoporosis. Many of these disorders are generically referred to as male menopause.

Several forms of testosterone therapy exists in the United States today. Recently, transdermal preparations have gained favor in the market. However, a scrotal testosterone patch results in supraphysiologic levels of 5α-dihydrotestosterone (DHT) due to the high concentration of 5α-reductase in scrotal skin. It is not known whether these elevated DHT levels have any long-term health consequences. Nonscrotal systems are considered more convenient and most patients achieve average serum concentrations within the normal range and have normal levels of DHT. Oral testosterone therapy is not recommended because doses required for replacement therapy are associated with significant risk of hepatotoxicity.

SUMMARY

The present invention is related to methods of administering compositions comprising 0% to 29% weight/weight of (cis, -Z-, trans-clomiphene) (hereinafter "cis-clomiphene") and 100% to 71% w/w (trans-, E-, cis-clomiphene) (hereinafter "trans-clomiphene") or pharmaceutically acceptable salts thereof. The compositions may consist essentially of trans-clomiphene or an analog thereof.

The compositions may be administered to a patient in a single dose that results in a pharmacologically effective blood concentration of testosterone over a period of time from 3 to 30 days. The single dose may be from about 5 to about 100 mg. The single dose may also be from about 12.5 to about 50 mg. The single dose may also 12.5, 25 or 50 mg. The period of time may be from about 7 to about 15 days. The period of time may also be from about 10 to about 12 days.

The compositions may be administered to a patient that is in need of increased testosterone levels. The compositions may also be administered to a patient that is in need of reduced cholesterol levels. The compositions may also be administered to a patient that is in need of increased muscle mass. The compositions may also be administered to a patient that suffers from lipodystrophy. The compositions may also be administered to a patient that is in need of increased lymphocyte levels. The compositions may also be administered to a patient in need of reduced triglyceride levels. The compositions may also be administered to a patient that suffers from benign prostate hypertrophy. The compositions may also be administered to a patient that suffers from prostate cancer. The compositions may also be administered to a patient that suffers from a disorder related to male hypogonadism. The disorder related to hypogonadism may be reduction of muscle mass. limitation of body performance capacity, reduction of bone density, reduction of libido, reduction of potency, reduction of benign prostatic hyperplasia or infertility.

DETAILED DESCRIPTION

The present invention provides dosing procedures for increasing testosterone levels in male mammals and for ameliorating or preventing the sequelae of low testosterone levels. The present invention is based on the surprising discovery that after cessation of treatment with compositions comprising trans-clomiphene, there is a persistence of increased levels of testosterone, LH and FSH in the serum. Based on the prolonged effects, compositions comprising trans-clomiphene may be administered intermittently or some other non-daily fashion and still achieve therapeutic effects.

Figure 2:
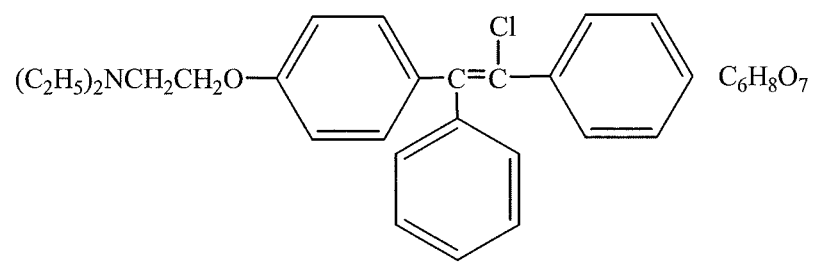
FIG. 2 shows the chemical structure of clomiphene citrate.

Clomiphene (FIG. 2) is an antiestrogen related to tamoxifen that blocks the normal estrogen feedback on the hypothalamus and subsequent negative feedback on the pituitary. This leads to increases in luteinizing hormone (LH) and follicle stimulating hormone (FSH). In men, these increased levels of gonadotropins stimulate the Leydig cells of the testes and result in the production of higher testosterone levels. Clomiphene citrate has the following structure:

Ernst et al., J. Pharmaceut. Sci. 65:148 (1976), have shown that clomiphene is a mixture of two geometric isomers which they refer to as cis, -Z-, clomiphene (cis-clomiphene or zuclomiphene) and trans-, E-, clomiphene, (trans-clomiphene or enclomiphene). According to Ernst, et al. trans-clomiphene HCl has a melting point of 149° C.-150.5° C., while cis-clomiphene HCl has a melting point of 156.5° C.-158° C.

Ernst et al. have also noted that (the trans-isomer) is anti-estrogenic (AE) while the cis-isomer is the more potent and more estrogenic form and has also been reported to have anti-estrogenic activity. The authors attribute the effect of the drug on ovulatory activity to both forms stating that the mixture is more effective than trans-clomiphene alone. The trans-isomer aids ovulation at the level of the hypothalamus. The estrogenic isomer cis-clomiphene contributes to enchanced ovulation elsewhere in the physiologic pathway leading to ovulation. The isomers are also reported to have different in vivo half-life. Furthermore the cis form has been reported to leave residual blood levels for in excess of one month following a single dose.

Vandekerckhove, et al. (Cochrane Database Syst Rev 2000; (2):CD000151 (2000)) noted that ten studies involving 738 men have suggested that anti-estrogens appear to have a beneficial effect on endocrinal outcomes, i.e. testosterone, but there is not enough evidence to evaluate fertility effects. Nevertheless should clomiphene administration enhance testosterone levels then one could easily conclude that the drug should positively impact the side effects of testosterone deprivation as long as the testes still retain the ability to respond to gonadotropin stimulation.

Clomiphene is currently approved as a mixture of both cis- and trans-isomers, the cis-isomer being present as about 30% to 50% (Merck Manual) for fertility enhancement in the anovulatory patient. Clomiphene improves ovulation by initiating a series of endocrine events culminating in a preovulatory gonadotropin surge and subsequent follicular rupture. The drug is recommended to be administered for 5 days at a dose of up to 100 mg daily. Clomiphene has also been associated with numerous side effects including: blurred vision, abdominal discomfort, gynecomastia, testicular tumors, vasomotor flushes, nausea, and headaches. Furthermore, other studies suggest that clomiphene possesses both genotoxic and tumor enhancement effects. The net outcome of these observations is that clomiphene in its current format, having between 30% and 50% of the cis isomer, would be unacceptable for chronic therapy in men for the treatment of testosterone deficiency.

Clomiphene has also been used for therapeutic intervention in men with low testosterone levels. Tenover et al., J. Clin. Endocrinol. Metab. 64:1103, (1987) and Tenover et al., J. Clin. Endocrinol. Metab. 64:1118 (1987) found increased in FSH, LH in both young and old men after treatment with clomiphene. They also found increases in free and total testosterone in men with young men showing significant increases Studies were also conducted to determine whether or not clomiphene could be used to improve fertility in men by improving semen quality. Homonnai et al. Fertil. and Steril 50:801 (1988) saw increases in sperm concentration and count but others have not. (See e.g., Sokel, et al., Fertil. and Steril. 49:865 (1988); Check, et al., Int. J. Fertil. 34:120 (1989); Purvis, et al., Int. J. Androl 21:109 (1989); and Breznik, Arch. Androl. 21:109 (1993).) One group saw a deterioration in the percentage of normal sperm with long-term treatment. Shamis, et al., Arch. Androl 21:109 (1991). A WHO study showed no changes in semen quality or fertility after 6 months of treatment. (Anonymous Androl. 15:299 (1992).) A meta-analysis seems to confirm that testosterone levels go up in men with poor quality sperm but not fertility. (Vanderkerckhove, et al., 2000). Studies have also suggested that long term treatment with clomiphene does not seem to have a drastic deleterious effect on health, although it did show that treatment resulted in poorer sperm quality after 4 months. Studies have kept men on clomiphene for as long as 18 months and at levels of 25 mg per day or 100 mg every other day.

In 1991, Guay et al (Urology 38:377 (1991)) suggested that clomiphene could treat sexual dysfunction in men. Their hypothesis seems to be that sexual function follows testosterone levels. This was supported by early studies showing positive influence of androgens and sexual function, Davidson, et al., J. Clin. Endocrinol. Metab. 48:955 (1979), and studies that rated sleep-related erections as a strong response to T, Cunningham, et al., J. Clin. Endocrinol. Metab. 70:792 (1990). However, in 1995, Guay et al. (Gray, et al., J. Clin. Endocrinol. Metab. 80:3546 (1995)) published a study in which they saw increase in LH, FSH, and testosterone after 2 months of clomiphene but no effects on erectile dysfunction. There might be some advantage for young men and specific groups of older men, but it seems that just raising the testosterone level is not enough. Effects of testosterone on sleep-related erections may have been taken too seriously (Herskowitz, et al., J. Psychosomat. Res. 42:541 (1997)).

According to the present invention, a composition comprising of one isomer preferably trans-clomiphene or a predefined blend of the isomers of clomiphene as described below differing from the normally produced mixture are used to enhance testosterone levels while reducing the side effects of the drug. Thus, the present invention provides an oral therapy for increasing testosterone levels, which lacks or has diminished side effects connected with the existing clomiphene formulations.

In one embodiment of the present invention, a patient who has a need or desire to increase their serum testosterone levels are administered one or more dosages of an effective amount of composition comprising trans-clomiphene at a dosage between one mg to about 200 mg (although the determination of optimal dosages is with the level of ordinary skill in the art). Cis-clomiphene may also be present in the composition so long as the ratio of trans-clomiphene to cis-clomiphene is greater than 1. Analogs of the trans- and cis-isomers of clomiphene such as those described in Ernst, et al. supra are also useful in the practice of the present invention.

In another embodiment of the present invention, a patient suffering from a disorder related to hypogonadism is administered one or more dosages of an effective amount of composition comprising trans-clomiphene at a dosage between one mg to about 200 mg (although the determination of optimal dosages is with the level of ordinary skill in the art). Cis-clomiphene may also be present in the composition so long as the ratio of trans-clomiphene to cis-clomiphene is greater than 1. Analogs of the trans- and cis-isomers of clomiphene such as those described in Ernst, et al. supra are also useful in the practice of the present invention. The condition associate with hypogonadism includes, but is not limited to, reduction of muscle mass, limitation of body performance capacity, reduction of bone density, reduction of libido, reduction of potency, benign prostatic hyperplasia, oligospermia or azoospermia, absence or regression of secondary sexual characteristics, reduction of muscle mass, fatigue, depression and infertility. The compositions of the present invention may be used to treat patients suffering from other disorders including, but not limited to, the conditions described in U.S. application Ser. Nos. 10/427,768 (filed Apr. 3, 2003), 10/712,546 (filed Nov. 12, 2003), 60/588,223 (filed Jul. 14, 2004), 60/588,130 (filed Jul. 14, 2004) and 60/588,223 (filed Jul. 14, 2004)

Figure 1:
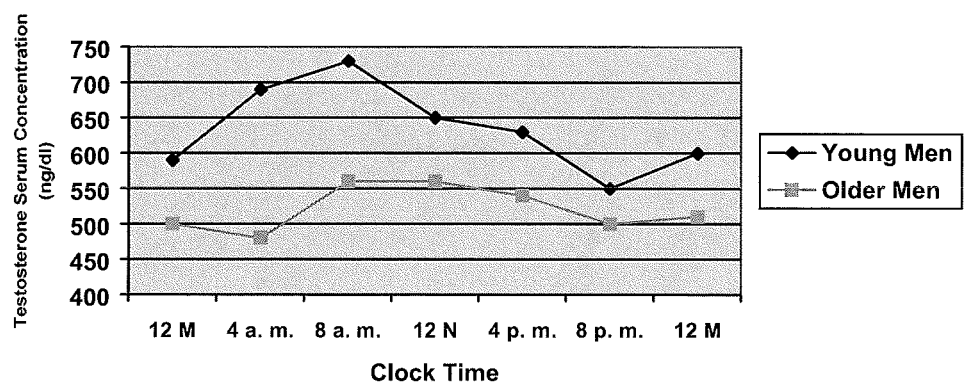
FIG. 1 is a graphic representative of the normal secretory total serum testosterone profiles in healthy men (young and old).

Dosages are preferably (but not necessarily) administered as part of a dosage regimen designed to give rise to serum testosterone levels that mimic or correspond to the normal secretary total serum testosterone profile described in FIG. 1. For example, according to FIG. 1 a dosage of the preferred composition may be administered in a pharmaceutical formulation that would give rise to peak serum testosterone levels at around 8 a.m. Such pharmaceutical formulations may be in the form of sustained release formulations prepared as described for example in U.S. Pat. No. 6,221,399, Japanese patent 4-312522, Meshali et al, Int. J. Phar. 89:177-181 (1993), Kharenko et al, Intern. Symp. Control Rel. Bioact. Mater. 22:232-233 (1995), WO 95/35093, Dangprasit et al., Drug. Devel. and Incl. Pharm. 21 (20):2323-2337 (1995); U.S. Pat. Nos. 6,143,353, 6,190,591, 6,096,338, 6,129,933, 6,126,969, 6,248,363 and other sustained release formulations well known in the art. The dosage of trans-clomphene may be from 5 to 100 mg. The dosage of trans-clomphene may also be from 12.5 to 50 mg. The dosage of trans-clomphene may also be 12.5 mg, 25 mg or 50 mg.

Based on the extended effect of a composition comprising trans-clomiphene, as shown herein, the dosage may be administered once per period of 3-30 days and achieve an equivalently beneficial effect as if the composition were administered on a daily basis. The dosage may also be administered once per period of 7-15 days or 10-12 days.

Suitable pharmaceutical compositions or unit dosage form may be in the form of solids, such as tablets or filled capsules or liquids such as solutions suspensions, emulsions, elixirs or capsules filled with the same, all for oral use. The compositions may also be in the form of sterile injectable solutions or emulsions for parenteral (including subcutaneous) use. Such pharmaceutical compositions and unit dosage forms thereof may comprise ingredients in conventional proportions.

Compositions according to the present invention may also be administered by the intravenous, subcutaneous, buccal, transmucusal, intrathecal, intradermal, intracisternal or other routes of administration. After administration of the composition serum testosterone levels may be measured as described above and dosages may be altered to achieve a sufficient increase in the serum testosterone levels to achieve the desired physiological results associated with normal testosterone described above. The compositions may be administered daily, non-daily or episodic. For example, the compositions may be administered at a dosing regime of 1, 2, 3, 4, 5, 6, 7, 8, 9, 10, 11, 12, 13 or 14 days between administrations.

All of the references discussed herein are incorporated by reference in their entirety.

The following Example is meant to be illustrative of the invention and is not intended to limit the scope of the invention as set out is the appended claims.

Example 1

Effects of Clomids on Serum Testosterone and Cholesterol in Male Baboons

Adult, male, Baboons were given 1.5 mg/kg of Clomid, Enclomid (trans-Clomid) or Zuclomid (cis-Clomid) for 12 consecutive days. The samples analyzed were sera taken on the day of first treatment before being given test article (day 0), after 12 days of treatment (day 12) and 7 days after the last treatment (end or wash-out).

1. Effects on Body Weight and Serum LH, FSH, PRL and Testosterone

Figure 3:
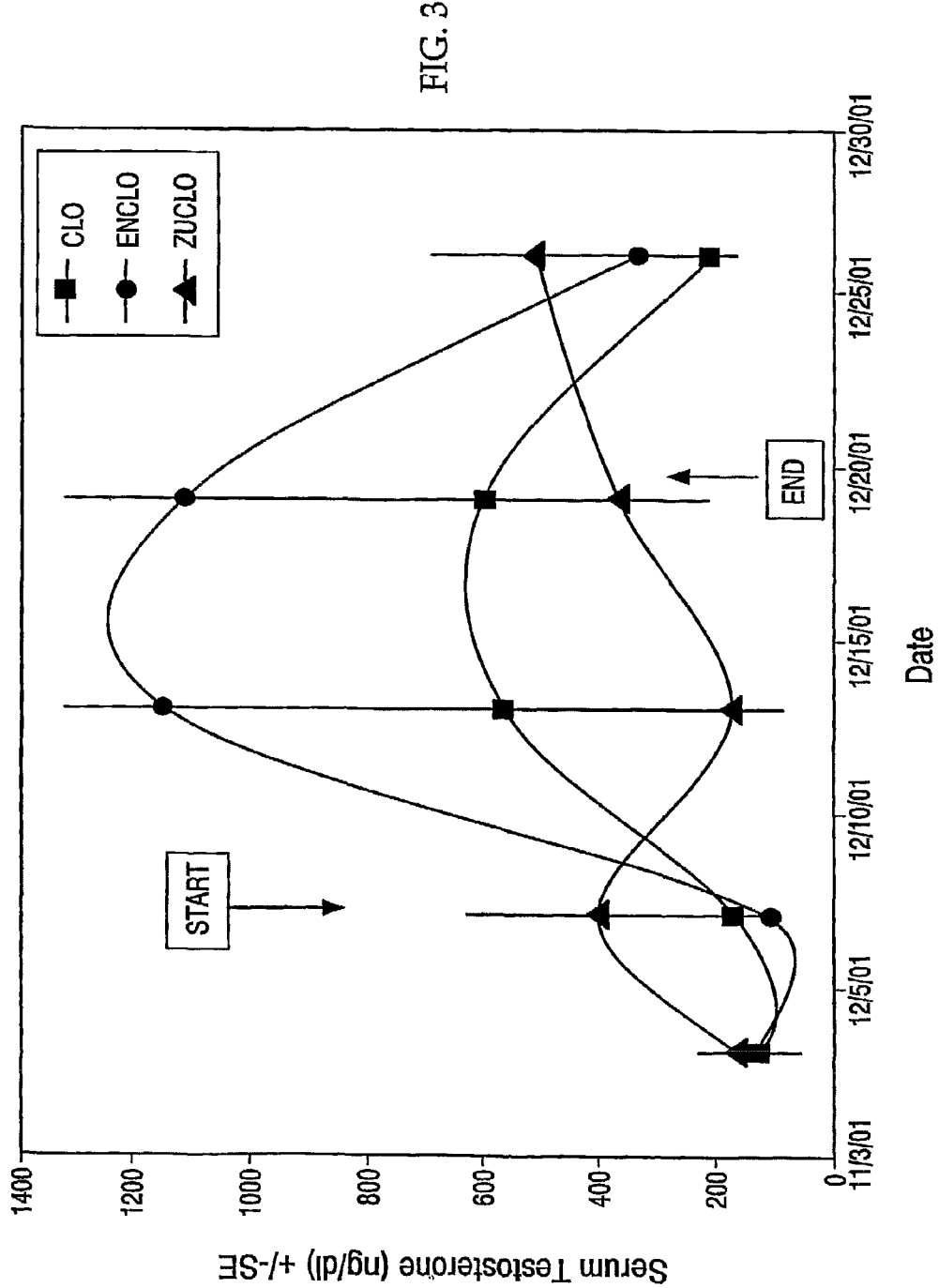
FIG. 3 is a graphic demonstration of the time course of serum testosterone levels with Clomid, Enclomid and Zuclomid.
Figure 4:
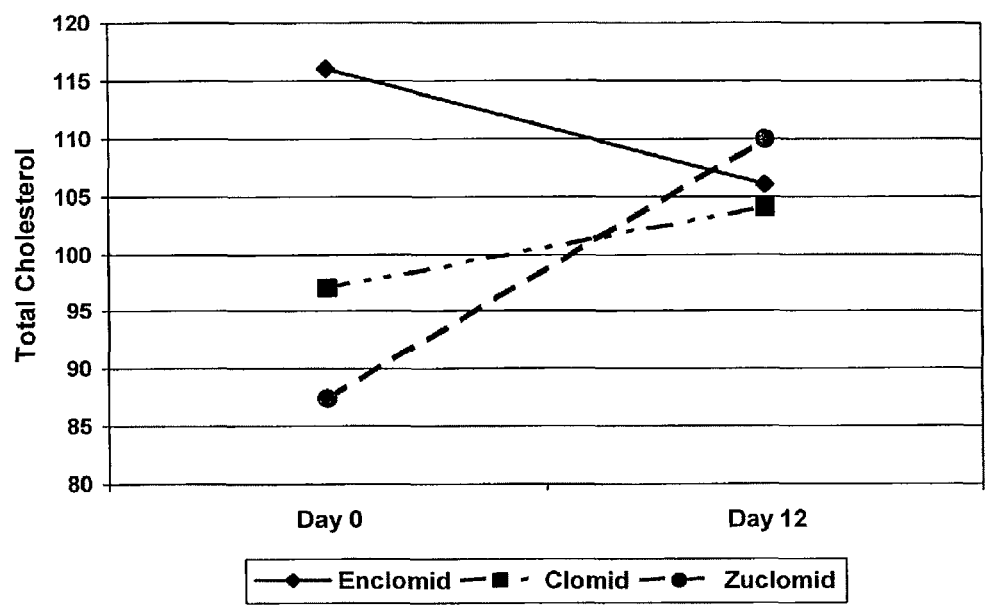
FIG. 4 is a graphic demonstration of the time course of cholesterol levels in baboon males treated with Clomid, Enclomid and Zuclomid.

There were significant increases in total serum testosterone in the group receiving Enclomid. See Table 1. There were no differences among groups in the baseline period or at day 0. There were also no differences among the three groups 7 days after treatment (the washout period). However, Enclomid produced higher levels of testosterone compared to Clomid and Zuclomid on day 6 (p=0.03 and p=0.00002 respectively) and compared to Zuclomid on day 12 (p=0.047). Zuclomid clearly did not raise total serum testosterone to any extent. Compared to the animals receiving Enclomid, the animals receiving Clomid exhibited more variable total testosterone levels on day 6 and later as judged by their coefficients of variations. When we looked at the time course of the effects (FIG. 3), we determined that only Enclomid significantly and statistically raised total serum testosterone on days 6 and 12 compared with either baseline or day 0 values. Moreover, cessation of Enclomid treatment, resulted in a significant drop in the level of total serum testosterone between day 12 and day 18 (washout). This indicates that Enclomid is readily cleared from the circulation consistent with the metabolic clearance seen for Enclomid in humans. Enclomid was clearly better and more consistent than Clomid itself and Zuclomid was ineffective.

TABLE 1

Serum Testosterone Levels (ng/dl)

| Group | ID | baseline Dec. 3, 2001 | 0 day Dec. 7, 2001 | 6 days Dec. 13, 2001 | 12 days Dec. 20, 2001 | wash-out Dec. 26, 2001 |
|---|---|---|---|---|---|---|
| CLO | 7500 | 79.01 | 76.15 | 940.97 | 891.5 | 150.9 |
| | 9012 | 97.55 | 305.24 | 585.92 | 555.6 | 316.3 |
| | 9097 | 158.06 | 102.94 | 151.12 | 318.9 | 143.6 |
| | mean | 111.5 | 161.4 | 559.3 | 588.7 | 203.6 |
| | SD | 41.3 | 125.2 | 395.6 | 287.7 | 97.7 |
| ENCLO | 7223 | 64.57 | 74.96 | 1223.8 | 633.6 | 307.2 |
| | 8021 | 166.86 | 133.59 | 1128.2 | 1466 | 399.2 |
| | 8369 | 170.45 | 106.47 | 1081.1 | 1166 | 271 |
| | mean | 134.0 | 105.0 | 1144.4 | 1088.5 | 325.8 |
| | SD | 60.1 | 29.3 | 72.7 | 421.6 | 66.1 |
| ZUCLO | 7438 | 124.84 | 210.4 | 137.51 | 314.5 | 359.7 |
| | 8292 | 104.66 | 67.37 | 169.98 | 406.1 | 860.5 |
| | 10098 | 282.29 | 904.82 | 227.95 | 353.0 | 274.1 |
| | mean | 170.6 | 394.2 | 178.5 | 357.9 | 498.1 |
| | SD | 97.3 | 448.0 | 45.8 | 46.0 | 316.8 |
| | ANOVA | p = 0.61 | p = 0.43 | p = 0.007 | p = 0.57 | p = 0.256 |
| | K-W | p = 0.56 | p = 0.84 | p = 0.051 | p = 0.079 | p = 0.252 |

There were no changes in serum LH or FSH. The ratio of total serum testosterone to LH followed the same pattern as total serum testosterone, suggesting a lack of dependence (data not shown). There was also no change in body weight during the 12 day study. There was a decrease in serum prolactin (PRL) during the study in the group receiving Enclomid, suggesting an effect of antiestrogen that has been described in part (Ben-Jonathan and Hnasko, 2001) and expected on the basis of the fact that as men age, testosterone declines and Prolactin increase (Feldman et al., 2002).

2. Effects on Cholesterol Levels

Treatment with Enclomid tended to decrease serum cholesterol and Zuclomid tended to increase the same parameter. Preliminary analysis indicated that the changes in cholesterol levels were not statistically significant and that the changes were within the normal range. Due to the observed trend for the two isomers to demonstrate opposite effects on cholesterol levels over a short period of time, further analysis was conducted.

Detailed analysis indicated that Enclomid resulted in an 8% decrease in serum cholesterol levels. Conversely, treatment with Zuclomid resulted in a 22% increase in serum cholesterol levels. Treatment with Clomid resulted in a slight increase in serum cholesterol levels. The opposite effect of Enclomid and Zuclomid on serum cholesterol levels is not unexpected given that the isomers have, alternatively, estrogen agonist or antagonist activity. These results indicate that Enclomid may be used for treating patients with high cholesterol levels. These results also indicate that Enclomid may be more benign than Zuclomid with respect to serum cholesterol if used chronically for increasing testosterone levels.

3. Effects on Clinical Chemistry Parameters

The mean values for each parameter did not differ among the three groups for any test parameter at the beginning of the study as determined by ANOVA or by the Kruskal-Wallis test. All groups exhibited normal values at each parameter except for (1) serum sodium; a related calculated parameter, anionic gap, which were low for all nine baboons throughout the trial; (2) serum glucose; and (3) BUN which were high on day 0 for the group which would be treated with Enclomid. On day 12 of treatment and 7 days after treatment (washout), there were no differences among groups for any parameter except anionic gap that showed that the Clomid and Zuclomid groups had lower values than the Enclomid group. The values of serum sodium and anionic gap appear to be anomalies associated with this group of baboons.

There were substantive effects on the red blood cell population with Enclomid and Zuclomid and on hematocrit with Zuclomid. All the compounds lower the mean cell hemoglobin concentration (MCHC) either at day 0 or at the endpoint. With no change in mean cell hemoglobin (MCH) and an increase in the mean cell volume (MCV), the lowering of MCHC is predictable. Although testosterone might be expected to raise hematocrit, only Zuclomid treatment, which did not increase total serum testosterone, demonstrated a statistical difference. Clearly, men in a clinical trial that uses Zuclomid should be monitored for the characteristics of their red blood cell population. Enclomid would be predicted to have less of an effect.

There appears to be a clear effect of 12-day Enclomid treatment on platelets although the values found stayed within the normal range. One thing to consider here is the sexual dimorphism in platelet counts between male and female baboons (279 for males vs. 348 for females). This is likely to be due to hormones. Since the Enclomid group demonstrated increased testosterone, the lowering of the platelet count could be secondary to the change in testosterone in this group. Moreover, treatment with Enclomid pushed the platelet count to its normal male level from a day 0 level that was the high end of the normal range for this group. Enclomid would not necessarily predict a deleterious effect on platelets.

All the Clomids tested had effects on the white blood cell (WBC) population, the most striking was that of Enclomid on raising the counts of lymphocytes and eosinophiles. The effects are not as straightforward as they would seem to be. There appears to be a strong effect of Enclonud on lowering the percent of granulocytes in the blood. The effects are very strong after the 7-day washout period when the values are decreased below the normal range. (This time course could reflect the relatively long time required to affect change the WBC population.) There is little sexual dimorphism in baboons with respect to the white blood cell populations, so the effects are more likely to be due to the compound itself than changes in testosterone. However, when we look at the calculated count of granulocytes using the WBC count, we find no differences in granulocyte count due to any compound. Concomitantly, it is the lymphocyte story that is the most interesting. Both the count and percent lymphocytes in the population increase with Enclomid treatment. Whereas the mean values of percent lymphocytes remain in the normal range, given the trend for an increase in WBC count, the net effect is an increase in lymphocyte count with Enclomid. This eosinophil result is analogous. There is a clear implication for treating men who have low lymphocytes, such as men who are HIV-positive. Since Enclomid is unlikely to lower lymphocytes based on this result, a case could be made for its use in the population of men with AIDS. These individuals are often treated with agents that are intended to raise testosterone due to the wasting effects of disease. Low liver and kidney toxicity and favorable effects on cholesterol and lipids are also highly favored attributes for any medication intended for use HIV-positive men who are already compromised by their disease.

The increase in serum glucose with Clomid or Zuclomid was within the normal range. In the case of Enclomid where the mean serum glucose values were high on day 0, there were no increases with treatment. There was no evidence that Enclomid would have a deleterious effect on blood glucose.

No clearly adverse effects on liver function are apparent as judged by the enzymes AST and ALT. The trend in these values was a decrease with treatment. An increase in the level of enzymes in the serum would indicate liver damage. ALT/SGPT was out of range low at the end of the study for the Clomid group although the differences over the treatment period were not statistically significant. The changes with Enclomid and Zuclomid were within the normal range. AST is depressed in pregnancy; thus the action of an estrogen agonist such as Zuclomid in lowering the marginal AST level could be rationalized. Alkaline phosphatase (ALP) is also found in the liver and is elevated various disease states. The lowering of ALP argues further against hepatic damage. There were no changes in serum albumin, also a liver product. A strong suppression of serum albumin over an extended time period could contribute to free serum steroid hormone levels in humans although a more important role is played by sex hormone binding globulin. As a bottom line, none of the compounds could be linked to liver damage on the basis of the parameters assayed.

Osteoblastic activity and diseases of the bone are accompanied by high serum ALP values. ALP was not elevated following Zuclomid treatment and was decreased in value following Enclomid treatment. The trends would predict a more benign result for the use of Enclomid compared to Zuclomid.

Although BUN and BUN/creatinine were altered during the study in the Clomid and Enclomid groups, the lack of a definitive change in creatinine argues against renal dysfunction. A loss of glomerular filtration capacity would result in an increase in BUN. Decreased BUN occurs in humans due to poor nutrition (not likely in a controlled setting), or high fluid intake (presumably accompanied by edema). Also, despite an increase in total serum testosterone between day 0 and Day 12 with Enclomid, there were no differences between serum creatinine values, arguing against an increase in muscle mass over this short time interval.

Serum sodium levels were lower than reference values for all animals throughout the study. Serum carbon dioxide was higher than reference values on day 12 for the Clomid and Zuclomid groups. Serum anion gap was lower for all animals throughout the study, paralleling the sodium results. Enclomid raised this parameter towards normal values. The electrolyte imbalances detected in the test animals throughout all treatment periods remains elusive but might be part of the same fluid derangement phenomenon suggested by the BUN results.

The foregoing results indicate that Enclomid is more effective than Clomid or Zuclomid at enhancing total serum testosterone. Zuclomid is clearly not effective and that deficiency limits any use of Clomid for hypogonadism, particularly since the Zuclomid component of Clomid would predominate in the circulation over time given its longer half-life.

Enclomid appeared to be relatively benign in all aspects when compared to Zuclomid and, often, even Clomid. This is particularly true when consideration is given to the trend of Enclomid to lower cholesterol, and liver enzymes as opposed to Zuclomid's trend to raise the same parameters. The surprising trend for Enclomid to raise the lymphocyte count may be useful for men with AIDS if it can be shown the CD4+ subpopulation of lymphocytes is not lowered or is enhanced.

Example 2

Method for Increasing Testosterone Level in Men Using Trans-Clomiphene and Mixtures of Trans-Clomiphene and Cis-Clomiphene at Ratios Greater than 1

Prior to administration of trans-clomiphene, blood samples are taken from subject males and testosterone levels are measured using methodologies described for example in Matsumoto, et al. Clin. Endocrinol. Metab. 56; 720 (1983) (incorporated herein by reference). Sex hormone binding globulin (SHBG), both free and bound to testosterone, may also be measured as described for example in Tenover et al. J. Clin. Endocrinol. Metab. 65:1118 (1987) which describe measurement of SHBG by both a [$^3$H] dihydrotestosterone saturation analysis and by radioimmunoassay. Non-SHBG-bound testosterone levels (bioavailable testosterone) are also measured for example according to Tenover et al. J. Clin. Endocrinol and Metab. 65:1118 (1987). See also Soderguard et al. J. Steroid Biochem 16:801 (1982) incorporated herein by reference.

Patients are given daily dosages of 1.5 mg/kg clomiphene, wherein the ratio of trans-clomiphene to cis-clomiphene is greater than 1. Patients are monitored for testosterone levels such that the dosage amount and dosage frequency may be adjusted to achieve therapeutic levels of testosterone in the patient.

Example 3

Comparison of Androxal™ to Androgel®

A placebo controlled challenge study was conducted at the Advanced Biological Research, Inc. (ABR) Clinical Research Center in Hackensack, N.J. to compare orally administered Androxal™ (trans-clomiphene) to Androgel® in hypogonadal men. Androgel® (Solvay Pharmaceuticals, Inc.) consists of a cream that administers exogenous testosterone in a transdermal matrix.

The study enrolled 62 hypogonadal men with testosterone levels less than 300 ng/dl (normal 298-1034 ng/dl) that were randomized into 6 different arms, three doses of Androxal™ (12.5 mg, 25 mg, and 50 mg), placebo, and both high and low doses of Androgel®. Half of the men in each of the Androxal™ and placebo arms were randomized into cohorts that underwent in-clinic sessions on days 1 and 14 to determine pharmacokinetic parameters for Androxal™ as well as cyclical changes in testosterone. The placebo and Androxal™ doses were administered in a double blind fashion. The Androgel® cream was administered in an open label fashion. Half of the Androgel® patients underwent in-clinic sessions similar to the other patients in the study. Following the two week drug exposure patients were followed for an additional seven to ten days to determine the status of their testosterone levels. There were no side effects noted in either the Androxal™ or Androgel® arms of the study that were different than placebo.

1. Effects on Testosterone Levels

Figure 5:
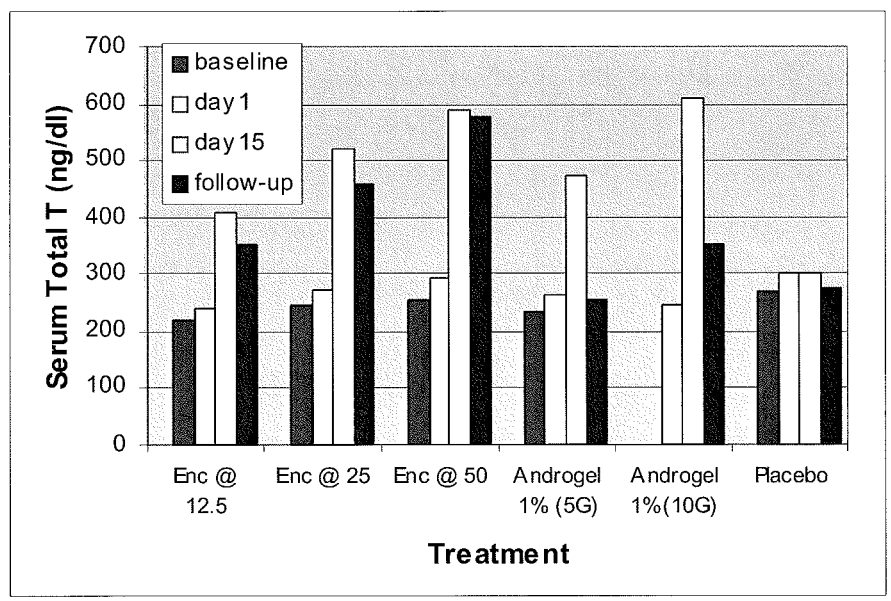
FIG. 5 demonstrates the effect of Androxal™ or Androgel® on testosterone levels.

All doses of Androxal™ or Androgel® produced statistically significant changes in testosterone from baseline testosterone levels (FIG. 5). The low, mid and high doses of Androxal™ achieved mean increases of 169, 247, and 294 ng/dl respectively, while those of Androgel® 5G, the lowest approved dose, and Androgel® 10G, the highest approved dose, produced changes from baseline that were 212 and 363 ng/dl. These values were statistically indistinguishable from those changes achieved with Androxal™. This inability to show differences between Androxal™ and Androgel® appears to result from the highly variable results found when Androgel® is used. For example the 50 mg dose of Androxal™ raised mean total testosterone to 589±172 ng/dl after 15 days, a coefficient of variation (CV) of 29% and similar to the placebo group (36%). On the other hand Androgel® 5G and 10G yielded mean total testosterone values 473±289 ng/dl and 608±323 ng/dl, CV's of 61% and 53% respectively.

After 14 days of Androxal™ therapy all doses were associated with a total testosterone diurnal pattern similar to the placebo group, i.e. a morning peak, a mid-day trough and a rise overnight. Without being bound by theory, this pattern may be due to the mode of action of Androxal™, which appears to be mediated through effects on the hypothalamic-pituitary axis as shown below. The diurnal pattern for men on Androgel® was nearly flat. However, spikes in total testosterone for Androgel® were associated with dosing and often exceeded the normal high level of 1,034 ng/dl. Certain individuals on Androgel® 10G were able to achieve peak levels of total testosterone of over 2500 ng/dl.

Interestingly, the level of serum total testosterone in the follow-up period (i.e., 7-10 days after cessation of daily oral treatment) unexpectedly remained high after treatment with Androxal™. In addition, the serum total testosterone levels were significantly higher at the highest dose of Androxal™ compared to the high dose of AndroGel® 1% (p=0.017, t-test).

2. Effects on LH and FSH Levels

Figure 6:
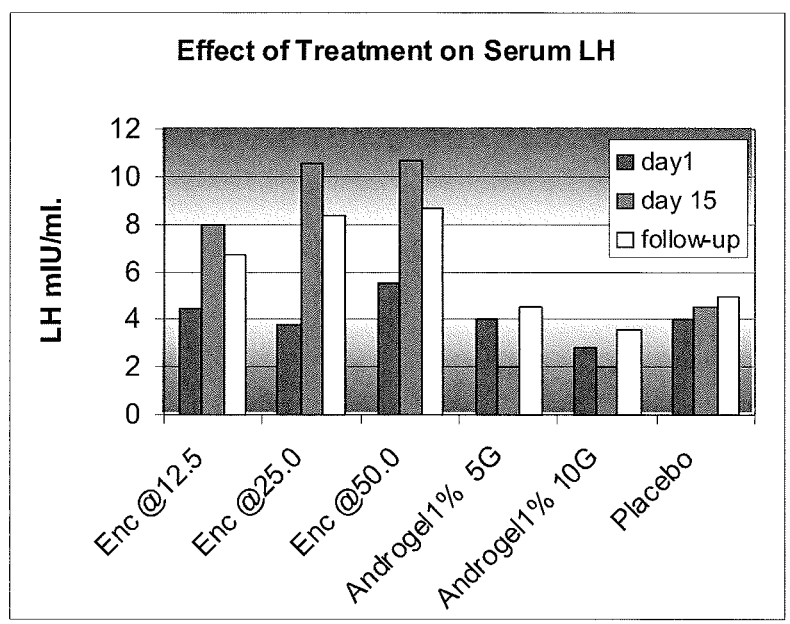
FIG. 6 demonstrates the effect of Androxal™ or Androgel® on LH levels.

Treatment with Androxal™ produced a statistically significant increase in the serum levels of LH in the hypogonadal male subjects (FIG. 6). As in the case of total serum testosterone there was an unexpected continuation in the level of serum LH in the follow-up period (i.e., 7-10 days after cessation of daily oral treatment) where those levels remained high for the three doses of Androxal™. By comparison, treatment with AndroGel® initially decreased LH and after cessation there was an apparent rebound towards pre-treatment levels.

Figure 7:
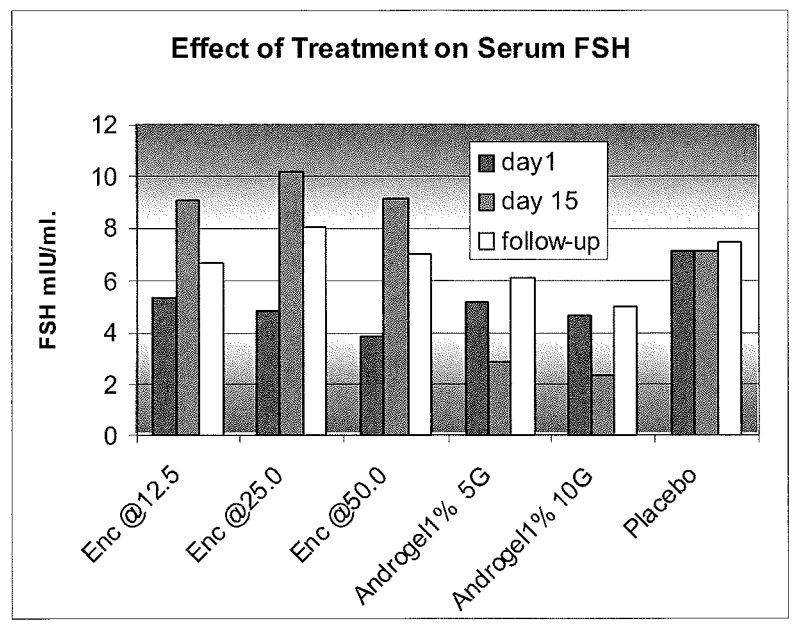
FIG. 7 demonstrates the effect of Androxal™ or Androgel® on FSH levels.

Treatment with Androxal™ also produced a statistically increase in the serum levels of FSH in the hypogonadal male subjects (FIG. 7). The pattern of increasing FSH is similar to that seen in the case of LH, that is, all doses of Androxal™ boosts serum FSH which remains high during the follow-up period whereas AndroGel® suppresses the level of serum FSH and cessation of treatment allows serum FSH to rebound towards concentrations more similar to pre-treatment levels.

3. Effects on Other Clinical Chemistry Parameters

The effect on serum dihydroxytestosterone (DHT) levels were also measured. Men on Androxal™ experienced a favorable shift in their DHT to total testosterone. For example men on the 50 mg dose of Androxal™ experienced a DHT/TT ratio of 0.83 as compared to the placebo group ratio of 1.07. By contrast the DHT/TT ratio for either of the Androgel® groups was >1.5. The results indicate that men on Androgel® were gaining DHT faster than total testosterone. Thus the normal levels of DHT was disrupted relative to testosterone in men on Androgel® therapy.

Results of clinical chemistry parameters also indicated, unexpectedly, that men on Androxal™ experienced a non-dose dependent reduction in triglycerides. The reduction in triglycerides averaged a decrease of 19.1% after two weeks of therapy. This compared to a 5.9% reduction for the placebo group and increases of 0.3% and 22% for the Androgel® 5G and 10G respectively.

4. Discussion

Based on this study we infer a number of potential advantages for Androxal™ as a potential therapy. Androxal™ appears to raise total testosterone into the normal range in a highly consistent manner without abnormally high spikes in serum testosterone. In addition, the use of transclomiphene to treat men that suffer secondary hypogonadism offers a new approach that potentially could offset one of the major side effects of exogenous therapies such as Androgel®. Exogenous therapies provide negative feedback thereby shutting down FSH and LH production. FSH is an essential reproductive hormone and in the male stimulates spermatogenesis. Long term exposure to exogenous testosterone, as a result of its effects on FSH production, causes a reduction in sperm synthesis, leading to the potential for transient infertility due to low sperm counts and therefore a resulting shrinkage of the testis, since the volume of the testis is related to the level of spermatogenesis within the seminiferus tubules. The increase in FSH levels also indicates that Androxal™ may be used to treat infertility in males, including hypogonadal males. Moreover, the extended affects of Androxal™ on serum testosterone, FSH and LH levels indicate that Androxal™ may be administered with altered dosages or scheduling, allowing perhaps even non-daily or episodic treatment.

The invention claimed is:

1. A method for treating secondary hypogonadism or a disorder related thereto in a human male in need of such treatment comprising daily administration of a composition consisting essentially of trans-clomiphene or a salt thereof to achieve a pharmacologically effective blood concentration of testosterone and thereafter a 3 to 30 day interval between at least two consecutive administrations.

2. The method of claim 1, wherein the dose is 5 to 100 mg trans-clomiphene.

3. The method of claim 2, wherein the dose is 12.5 to 50 mg trans-clomiphene.

4. The method of claim 3, wherein the dose is 12.5, 25 or 50 mg trans-clomiphene.

5. The method of claim 1 wherein the interval is 7 days.

6. The method of claim 1 wherein the interval is 14 days.

7. The method of claim 1 wherein the interval is 30 days.

8. The method of claim 1 wherein the disorder related to secondary hypogonadism is selected from the group consisting of reduction of muscle mass, limitation of body performance capacity, reduction of bone density, reduction of libido, reduction of potency, benign prostatic hyperplasia, oligospermia or azoospermia, fatigue, depression and infertility.

9. The method of claim 1 wherein the male is a fertile male and wherein fertility is maintained in the male.

10. The method of claim 1 wherein the salt of trans-clomiphene is the citrate salt.

* * * * *